United States Patent
Kikuyama et al.

(10) Patent No.: US 10,088,089 B2
(45) Date of Patent: Oct. 2, 2018

(54) ROTARY JOINT

(71) Applicant: NIPPON PILLAR PACKING CO., LTD., Osaka-shi, Osaka (JP)

(72) Inventors: Yoshinori Kikuyama, Osaka (JP); Osamu Suzuki, Osaka (JP)

(73) Assignee: NIPPON PILLAR PACKING CO., LTD., Osaka-Shi, Osaka (JP)

( * ) Notice: Subject to any disclaimer, the term of this patent is extended or adjusted under 35 U.S.C. 154(b) by 158 days.

(21) Appl. No.: 15/263,013

(22) Filed: Sep. 12, 2016

(65) Prior Publication Data
US 2017/0074445 A1 Mar. 16, 2017

(30) Foreign Application Priority Data
Sep. 14, 2015 (JP) .................................. 2015-180666

(51) Int. Cl.
*F16L 39/04* (2006.01)
*F16L 27/087* (2006.01)
*A61M 1/00* (2006.01)
*F16L 19/06* (2006.01)

(52) U.S. Cl.
CPC .............. *F16L 39/04* (2013.01); *A61M 1/00* (2013.01); *F16L 27/087* (2013.01); *F16L 19/06* (2013.01)

(58) Field of Classification Search
CPC ................................ F16L 27/087; F16L 39/04
USPC .................................................. 285/273, 275
See application file for complete search history.

(56) References Cited

U.S. PATENT DOCUMENTS

| | | | | |
|---|---|---|---|---|
| 2,877,026 A | * | 3/1959 | Payne | F16L 39/04 277/365 |
| 3,122,373 A | * | 2/1964 | Lee | F16J 15/38 277/368 |
| 3,923,133 A | * | 12/1975 | Chivari | F16D 25/06 137/580 |
| 4,422,676 A | * | 12/1983 | Sitabkhan | F16L 39/04 285/121.4 |
| 4,700,924 A | * | 10/1987 | Nelson | E21B 21/02 166/319 |
| 5,080,401 A | * | 1/1992 | Stich | F16L 27/087 285/190 |
| 2002/0017785 A1 | | 2/2002 | Omiya et al. | |

FOREIGN PATENT DOCUMENTS

| | | | | |
|---|---|---|---|---|
| DE | 4006257 A1 | * | 9/1990 | ............ F16L 27/087 |
| JP | 2002-22076 | | 1/2002 | |
| JP | 2004019912 A | * | 1/2004 | ............ F16L 27/087 |
| JP | 2004316775 A | * | 11/2004 | ............ F16L 27/087 |

* cited by examiner

*Primary Examiner* — David Bochna
(74) *Attorney, Agent, or Firm* — Lewis Roca Rothgerber Christie LLP (57) ABSTRACT

Provided is a rotary joint that allows a case body to be made compact. A rotary joint includes: a cylindrical case body having a plurality of first flow passages formed therein; a shaft body having a plurality of second flow passages formed therein; rolling bearings and provided in an annular space formed between the case body and the shaft body; a plurality of tubular members provided in the annular space and each having a third flow passage formed for connecting the first flow passage and the second flow passage; a first seal configured to prevent leak of a fluid flowing through the first flow passage and the third flow passage; and a second seal configured to prevent leak of a fluid flowing through the third flow passage and the second flow passage.

10 Claims, 4 Drawing Sheets

ROTARY JOINT

CROSS-REFERENCE TO RELATED APPLICATION

This application claims the priority benefit of Japanese patent application number 2015-180666 filed Sep. 14, 2015, the entire contents of which are incorporated herein by reference.

BACKGROUND

Technical Field

The present invention relates to a rotary joint.

Background Art

A rotary joint is used in relative rotation portions of various rotary apparatuses such as a semiconductor manufacturing apparatus, a medical apparatus, and an apparatus for food. The rotary joint includes a first member and a second member that rotate relative to each other, and it is necessary to cause a plurality of different types of fluids between these two members to flow through different passages. Thus, the rotary joint has a configuration in which a plurality of first flow passages are formed in the first member, a plurality of second flow passages are formed in the second member, and one first flow passage and one second flow passage are connected to each other in a one-to-one relation, for causing the fluids to flow therethrough (see, e.g., Japanese Laid-Open Patent Publication No. 2002-22076).

Figure 4:
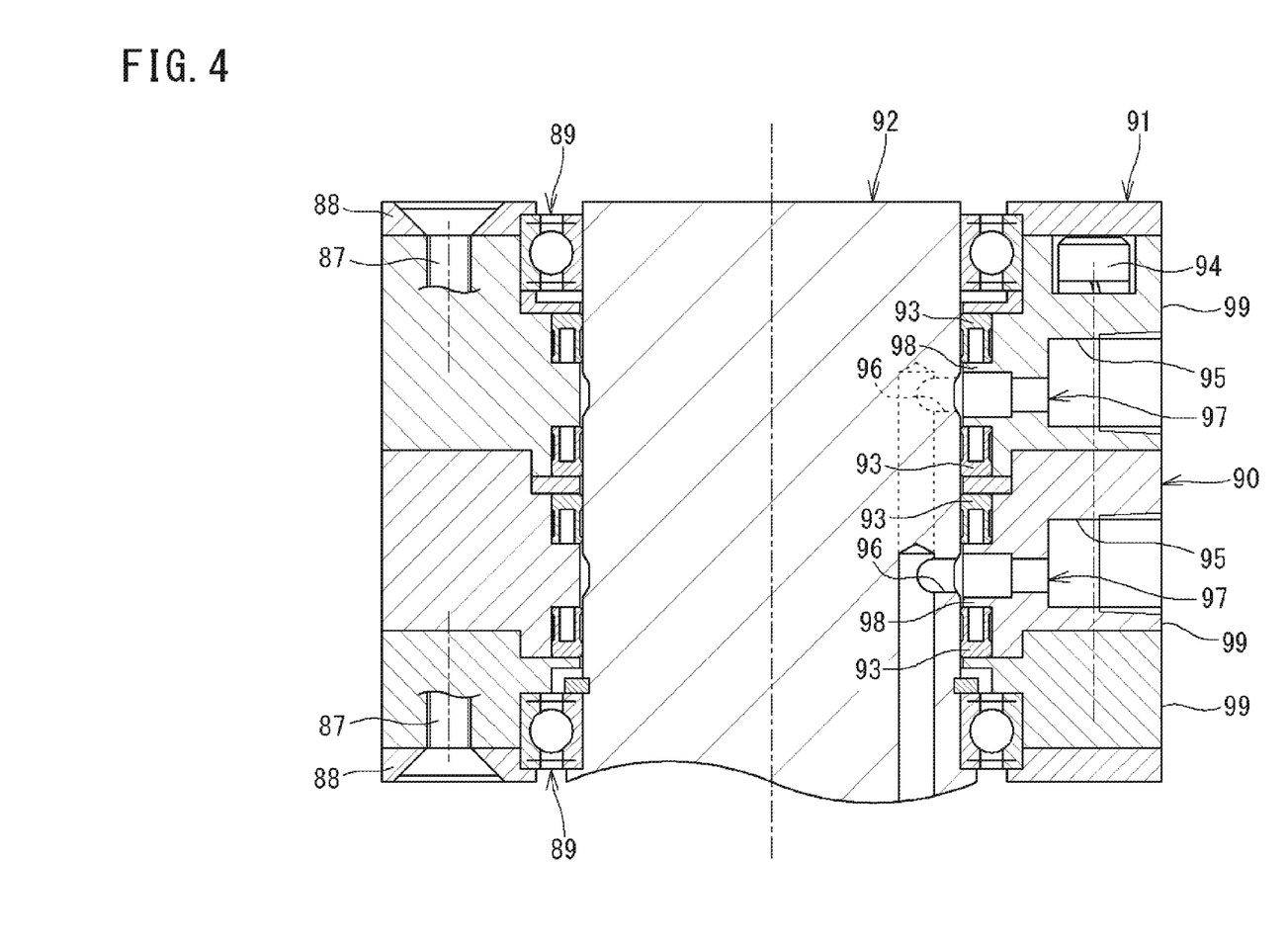
FIG. 4 is a cross-sectional view of a conventional rotary joint.

FIG. 4 is a cross-sectional view of a conventional rotary joint. The rotary joint 90 includes a cylindrical case body 91 (the above first member) and a shaft body 92 (the above second member) provided inside the case body 91. Upper and lower two first flow passages 95 are formed in the case body 91, and upper and lower two second flow passages 96 are formed in the shaft body 92. An opening of the upper first flow passage 95 and an opening of the upper second flow passage 96 are located at the same position in an axial direction, and these flow passages 95 and 96 are connected to each other to form a single flow passage 97. In addition, an opening of the lower first flow passage 95 and an opening of the lower second flow passage 96 are located in the same position in the axial direction, and these flow passages 95 and 96 are connected to each other to form a single flow passage 97. For preventing fluids flowing through the upper and lower flow passages 97, 97, respectively, from leaking to the outside, a plurality of seal rings 93 are provided between the case body 91 and the shaft body 92.

SUMMARY

Technical Problem

As shown in FIG. 4, the case body 91 is configured by a plurality of ring bodies 99 being aligned in the axial direction. This is because the plurality of seal rings 93 are incorporated between the case body 91 and the shaft body 92. That is, this is because the case body 91 has, in an radially inner region thereof, projection portions 98 in which portions of the first flow passages 95 are formed, so that, for providing the seal rings 93 adjacently to each projection portion 98 in the axial direction, it is necessary to stack and assemble another ring body 99 thereon each time the seal rings 93 are mounted adjacently to the projection portion 98.

Then, in the rotary joint 90, the plurality of ring bodies 99 are integrated with each other by means of a bolt 94.

As described above, in the conventional rotary joint 90, it is necessary to divide the case body 91 into the plurality of ring bodies 99 for assembling, and the (first) bolt 94 for integrating the plurality of ring bodies 99 is needed. Since the seal rings 93 are disposed in the radially inner region of the case body 91 (each ring body 99), a bolt hole (not shown) through which the bolt 94 is inserted is formed in a radially outer region of the case body 91 (each ring body 99).

Furthermore, for making the case body 91 and the shaft body 92 rotatable relative to each other, a pair of rolling bearings 89 are proved between the case body 91 and the shaft body 92, and annular members 88 are provided at both sides in the axial direction for preventing falling of the rolling bearings 89. The annular members 88 are fixed to the ring bodies 99 by means of second bolts 87, and serve as stoppers for the rolling bearings 89.

As described above, bolt holes for the second bolts 87 also need to be formed in the radially outer region of the case body 91 (each ring body 99), and the size of the case body 91 is increased in the radial direction for providing the second bolts 87 and the first bolt 94.

Therefore, an object of the present invention is to provide a rotary joint that allows a case body to be made compact.

Solution to Problem

A rotary joint according to the present invention includes: a cylindrical case body having a plurality of first flow passages formed so as to be opened in an inner peripheral surface thereof and at different positions in an axial direction; a shaft body provided inside the case body and having a plurality of second flow passages formed so as to be opened in an outer peripheral surface thereof and at different positions in the axial direction; a bearing portion provided in an annular space formed between the case body and the shaft body, the bearing portion supporting the case body and the shaft body such that the case body and the shaft body are rotatable relative to each other; a plurality of tubular members provided in the annular space and each having a third flow passage formed for connecting the first flow passage and the second flow passage; a first seal configured to prevent a fluid flowing through the first flow passage and the third flow passage from leaking through between the case body and the tubular member; and a second seal configured to prevent a fluid flowing through the third flow passage and the second flow passage from leaking through between the tubular member and the shaft body. The case body is composed of an integral and inseparable tube member that is longer in the axial direction than a dimension, in the axial direction, of an internal structure body including the bearing portion and the tubular members provided in the annular space so as to be aligned in the axial direction.

According to the present invention, the flow passage (third flow passage) that connects the first flow passage at the case body side and the second flow passage at the shaft body side is formed in each tubular member that is a member separate from the case body. Thus, even when the case body is not configured to have a divided structure as in the conventional art, that is, even when the case body is an integral and inseparable tube member, assembly of the rotary joint is enabled. Therefore, a bolt for integrating the case body as in the conventional art is unnecessary, so that it is possible to make the case body compact.

In addition, preferably, the rotary joint further includes a stopper detachably/mountably provided in the annular space, and relative movement, in the axial direction, of the shaft body and the case body between which the bearing portion and the tubular members are interposed is restricted in a state where the stopper is mounted, and is enabled in a state where the stopper is disengaged.

According to this configuration, in a state where the stopper is disengaged, the shaft body and the case body can be mounted by moving the shaft body and the case body relative to each other in the axial direction with the bearing portion and the tubular members interposed therebetween.

In addition, the second seal is preferably mounted in a recess portion formed in each tubular member. According to this configuration, it is possible to perform an operation of integrating the second seal with the tubular member to mount the second seal.

In addition, preferably, the first seal is an O-ring, an inclined surface is formed in each tubular member so as to be inclined relative to the inner peripheral surface of the case body, and the O-ring is mounted in a triangular cross-section space formed by the inclined surface, a portion of the inner peripheral surface of the case body, and a portion of a side surface of a member provided adjacently to the tubular member in the axial direction.

According to this configuration, the O-ring makes it possible to enhance a function to prevent each tubular member from rotating relative to the case body.

In addition, the second seal preferably includes an annular main body portion and an inner cylindrical lip portion and an outer cylindrical lip portion extending in the axial direction from a radially inner portion and a radially outer portion of the main body portion, respectively.

The second seal is easily moved in the axial direction along the outer peripheral surface of the shaft body to be easily mounted, and in a state where mounting of the second seal is completed, each tubular member which is integrated with the case body and the shaft body are rotatable relative to each other, but it is also possible to ensure sealability between each tubular member and the shaft body.

Advantageous Effects of Invention

According to the present invention, since the case body is composed of an integral and inseparable tube member, a bolt for integrating the case body as in the conventional art is unnecessary, so that it is possible to make the case body compact.

DETAILED DESCRIPTION OF EMBODIMENTS

Figure 1:
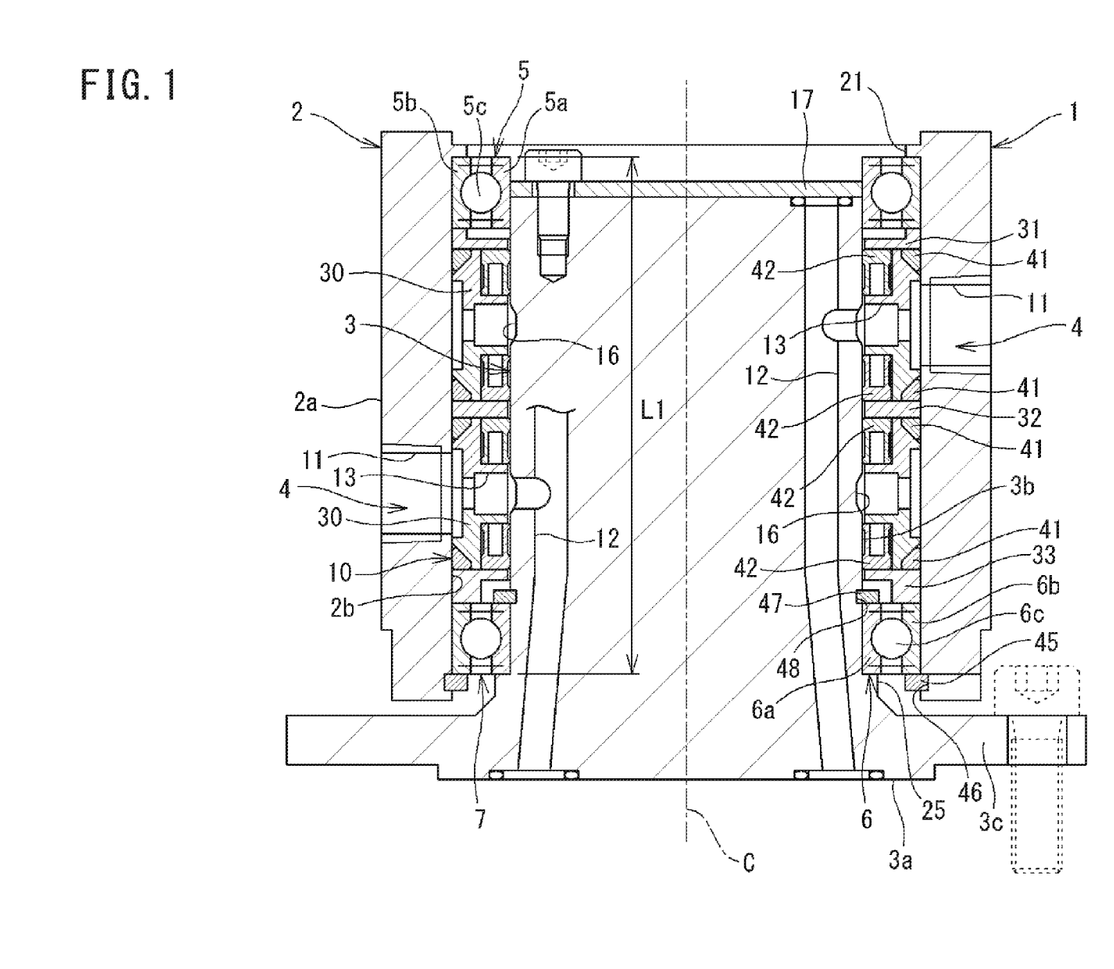
FIG. 1 is a longitudinal cross-sectional view of a rotary joint.

Hereinafter, an embodiment of the present invention will be described.
[Entire Configuration]
FIG. 1 is a longitudinal cross-sectional view of a rotary joint 1. The rotary joint 1 (hereinafter, also referred to as joint 1) includes a cylindrical case body 2 and a shaft body 3 provided inside the case body 2. The attitude of the joint 1 may be an attitude other than the attitude shown in FIG. 1. In the following description, the upper side in FIG. 1 is sometimes referred to as an "upper side" of the joint 1, and the lower side in FIG. 1 is sometimes referred to as a "lower side" of the joint 1. In addition, in the present embodiment, an axial direction is a direction along a center line C of the rotary joint 1 (also including a direction parallel to the center line C), and a center line of each of the case body 2 and the shaft body 3 coincides with the center line C.

An annular space 7 is formed between the case body 2 and the shaft body 3, and a bearing portion is provided in the annular space 7. The bearing portion of the present embodiment is rolling bearings 5 and 6, in particular, deep groove ball bearings. The rolling bearings 5 and 6 support the case body 2 and the shaft body 3 such that the case body 2 and the shaft body 3 are rotatable relative to each other.

In the joint 1, N (N is an integer not less than 2 and is 2 in the illustrated example) fluid passages 4 are formed. Each fluid passage 4 is formed by connecting one first flow passage 11 provided in the case body 2 and one second flow passage 12 provided in the shaft body 3 to each other via a later-described third flow passage 13. One fluid passage 4 is provided independently of the other fluid passage 4, and the joint 1 is configured so as to prevent a fluid flowing through one fluid passage 4 from being mixed with a fluid flowing through the other fluid passage 4.
[Shaft Body 3 and Case Body 2]

The shaft body 3 is composed of a linear member that is long in an up-down direction, and has a circular cross-section (transverse section). Two second flow passages 12 are formed in the shaft body 3. Each second flow passage 12 is opened at one side thereof in an end face 3a in the axial direction, and is opened at the other side thereof in an outer peripheral surface 3b. The second flow passages 12 are opened in the outer peripheral surface 3b and at different positions in the axial direction. That is, one of the second flow passages 12 is opened at an upper position, and the other second flow passage 12 is opened at a lower position. In addition, the second flow passages 12 of the present embodiment are opened at different positions also in a circumferential direction (positions away from each other by 180°). Moreover, recessed grooves 16 of which the number is equal to the number of the second flow passages 12 are formed on the outer peripheral surface 3b so as to be continuous in the circumferential direction, and each second flow passage 12 is opened in a portion of the recessed groove 16. A cover member 17 is mounted on an upper end portion of the shaft body 3 so as to close the second flow passages 12.

The recessed grooves 16 and a groove 48 for mounting a later-described snap ring 47 are formed on the outer peripheral surface 3b of the shaft body 3, and the other portion of the outer peripheral surface 3b is composed of a cylindrical surface that is straight along the axial direction. In particular, the outer peripheral surface 3b is a smooth machined surface subjected to machining.

The case body 2 is composed of a cylindrical member and has an inner peripheral surface 2b having a circular contour shape. Two first flow passages 11 are formed in the case body 2. Each first flow passage 11 is opened at one side thereof in an outer peripheral surface 2a and is opened at the other side thereof in the inner peripheral surface 2b. These first flow passages 11 are opened in the inner peripheral surface 2b and at different positions in the axial direction. That is, one of the first flow passage 11 is opened at an upper position, and the other first flow passage 11 is opened at a lower position. In addition, the first flow passages 11 of the present embodiment are opened at different positions also in the circumferential direction (positions away from each other by 180°). The first flow passages 11 are ports for connecting external pipes that are not shown.

In the case body 2, a projection portion 21 is provided at the inner peripheral side of an end portion at one side (an upper end portion) in the axial direction thereof so as to project radially inward. The projection portion 21 and a groove 46 for mounting a later-described snap ring 45 are formed on the inner peripheral surface 2b of the case body 2, and the other portion of the inner peripheral surface 2b is composed of a cylindrical surface that is straight along the axial direction. In particular, the inner peripheral surface 2b is a smooth machined surface subjected to machining. The case body 2 is composed of an integral and inseparable tube member that is long in the axial direction.

Due to the above, the annular space 7 is formed between the case body 2 and the shaft body 3 such that a cross-sectional shape of the annular space 7 is unchanged along the axial direction in a region other than the portions where the recessed grooves 16, the groove 48, the projection portion 21 and the groove 46 are formed. In addition to the rolling bearings 5 and 6, later-described tubular members 30, spacers 31, 32, and 33, first seals 41, and second seals 42 are provided in the annular space 7. These members provided in the annular space 7 are collectively referred to as an internal structure body 10.

[Internal Structure Body 10]

The upper rolling bearing 5 includes an inner ring 5a, an outer ring 5b, balls (rolling bodies) 5c interposed between the inner ring 5a and the outer ring 5b, and a retainer that retains the balls 5c and is not shown. The inner ring 5a is fitted and mounted on the outer peripheral surface 3b of the shaft body 3, and the outer ring 5b is fitted and mounted on the inner peripheral surface 2b of the case body 2. Movement of the rolling bearing 5 in the axial direction (toward the upper side in the axial direction) is restricted by the outer ring 5b being brought into contact with the projection portion 21 from the axial direction.

The lower rolling bearing 6 includes an inner ring 6a, an outer ring 6b, balls 6c interposed between the inner ring 6a and the outer ring 6b, and a retainer that retains the balls 6c and is not shown. The inner ring 6a is fitted and mounted on the outer peripheral surface 3b of the shaft body 3, and the outer ring 6b is fitted and mounted on the inner peripheral surface 2b of the case body 2. Movement of the rolling bearing 6 in the axial direction (toward the lower side in the axial direction) is restricted by the outer ring 6b being brought into contact with the snap ring 45 from the axial direction.

Each tubular member 30 is a circular member, has an inner diameter (slightly) larger than the outer diameter of the shaft body 3, and has an outer diameter (slightly) smaller than the inner diameter of the case body 2. The tubular members 30 of which the number is equal to the number of the fluid passages 4 are provided in the annular space 7. That is, two tubular members 30 are provided. The upper tubular member 30 is provided between the upper first flow passage 11 and the upper second flow passage 12, which are opened at the same position in the axial direction, and a third flow passage 13 for connecting this first flow passage 11 and this second flow passage 12 is formed in this tubular member 30. Similarly, the lower tubular member 30 is provided between the lower first flow passage 11 and the lower second flow passage 12, which are opened at the same position in the axial direction, and a third flow passage 13 for connecting this first flow passage 11 and this second flow passage 12 is formed in this tubular member 30.

Figure 2:
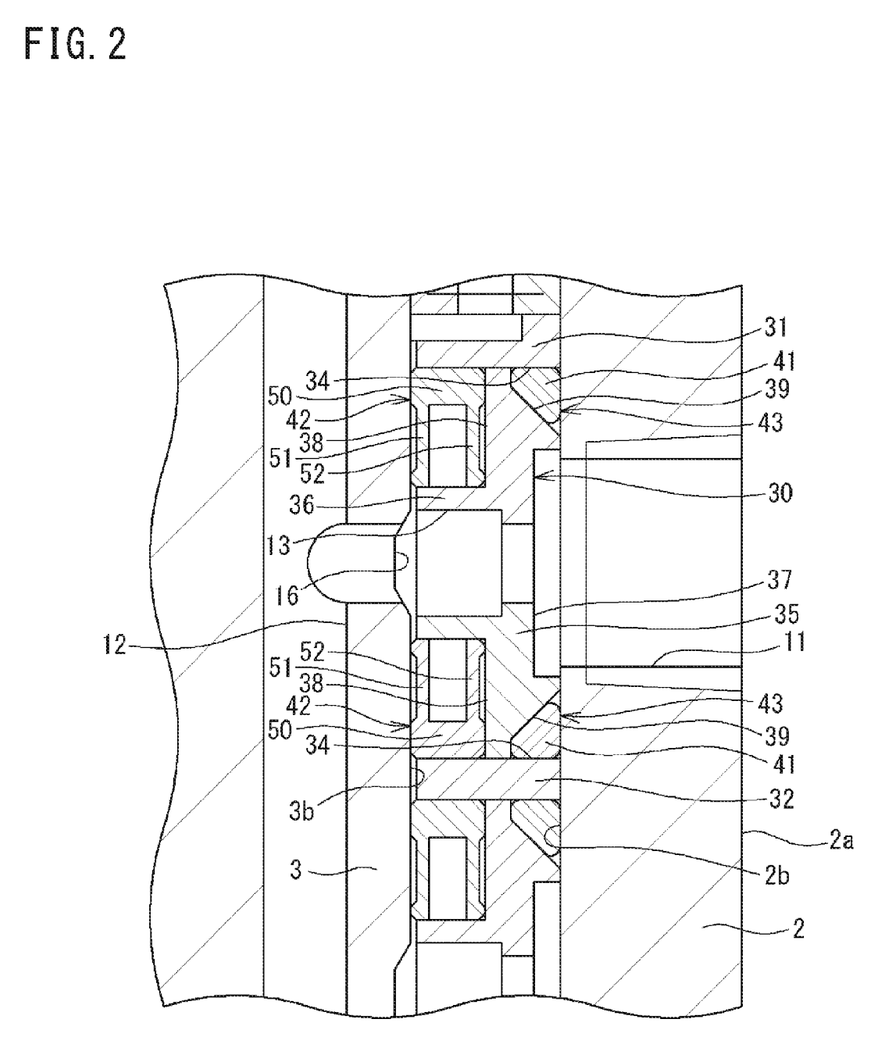
FIG. 2 is an enlarged view showing an upper tubular member and a peripheral area thereof.

FIG. 2 is an enlarged view showing the upper tubular member 30 and a peripheral area thereof. The tubular members 30 all have the same shape. Each tubular member 30 includes a cylindrical main body portion 35 and an annular raised portion 36 that projects radially inward from a center portion of the main body portion 35, and the third flow passage 13 is formed so as to penetrate the main body portion 35 and the raised portion 36. A groove 37 is formed at the outer peripheral side of the main body portion 35 so as to be continuous in the circumferential direction, and the third flow passage 13 is opened in a portion of the groove 37. In addition, the third flow passage 13 is opened at the radially inner side toward the recessed groove 16 formed in the shaft body 3. Accordingly, the first flow passage 11 is connected to the second flow passage 12 via the third flow passage 13.

The first seals 41, 41 are provided on outer peripheral portions of the tubular member 30 at both sides in the axial direction, and prevent a fluid flowing through the first flow passage 11 and the third flow passage 13 from leaking through between the case body 2 and the tubular member 30.

In addition, the second seals 42, 42 are provided on inner peripheral portions of the tubular member 30 at both sides in the axial direction, and prevent a fluid flowing through the third flow passage 13 and the second flow passage 12 from leaking through between the tubular member 30 and the shaft body 3.

Inclined surfaces 39 for mounting the first seals 41 are formed at both sides, in the axial direction, of the main body portion 35 of each tubular member 30. Each inclined surface 39 is composed of a tapered surface that is inclined relative to the inner peripheral surface 2b of the case body 2. Each first seal 41 is an O-ring. Each first seal (O-ring) 41 is mounted in a triangular cross-section space 43 that is formed by the inclined surface 39, a portion of the inner peripheral surface 2b of the case body 2, and a portion of a side surface 34 of a member provided adjacently to the tubular member 30 in the axial direction (the first spacer 31 at the upper side, the second spacer 32 at the lower side).

Annular recess portions 38 for mounting the second seals 42 are formed at both sides, in the axial direction, of the raised portion 36 of each tubular member 30. Each recess portion 38 has a shape opened toward two directions, that is, the inner side in the radial direction and the outer side in the axial direction.

Each second seal 42 is an elastic seal ring that includes an annular main body portion 50, an inner cylindrical lip portion 51, and an outer cylindrical lip portion 52. The inner cylindrical lip portion 51 and the outer cylindrical lip portion 52 have a cylindrical shape, and extend in the axial direction from a radially inner portion and a radially outer portion of the main body portion 50, respectively. In the second seal 42, the main body portion 50, the inner cylindrical lip portion 51, and the outer cylindrical lip portion 52 are made of polytetrafluoroethylene (PTFE), and a spring made of a metal is provided along the inner cylindrical lip portion 51 and the outer cylindrical lip portion 52, so that the second seal 42 has a self-sealing property. The material of the main body portion 50, the inner cylindrical lip portion 51, and the outer cylindrical lip portion 52 of the second seal 42 may be another fluorine resin or a material other than fluorine resins such as rubber materials.

As described above, a pair of the first seals 41, 41 are provided at the outer peripheral side of each tubular member 30, a pair of the second seals 42, 42 are provided at the inner peripheral side of each tubular member 30, and one unit is formed by the tubular member 30, the pair of the first seals 41, 41, and the pair of the second seals 42, 42. This unit is disposed between each first flow passage 11 and each second flow passage 12.

In FIG. 1, the first spacer 31, the second spacer 32, and the third spacer 33 are annular members, serve as spacers for disposing the tubular members 30 at desired positions in the axial direction, and also have a function for disposing and retaining the first seals 41 and the second seals 42 between the tubular members 30 and the spacers 31, 32, and 33. Each of the first spacer 31, the second spacer 32, and the third spacer 33 has an inner diameter (slightly) larger than the outer diameter of the shaft body 3 and has an outer diameter (slightly) smaller than the inner diameter of the case body 2.

In the annular space 7, the rolling bearing 5, the first spacer 31, the upper tubular member 30, which is provided together with the first and second seals 41 and 42, the second spacer 32, the lower tubular member 30, which is provided together with the first and the second seals 41 and 42, the third spacer 33, and the rolling bearing 6 are disposed in order from the upper side.

As described above, the rolling bearings 5 and 6 and the tubular members 30, etc. are provided in the annular space 7 so as to be aligned in the axial direction. The case body 2 is composed of an integral and inseparable tube member that is longer in the axial direction than a dimension L1, in the axial direction, of the internal structure body 10 including the rolling bearings 5 and 6 and the tubular members 30, etc. That is, the case body 2 is configured so as to be longer than the dimension in the axial direction from the upper rolling bearing 5 to the lower rolling bearing 6, and also the case body 2 is not divided and is composed of an integral tube member.

The rolling bearing 6 is brought into a state where the rolling bearing 6 is interposed in the axial direction between the snap ring 47 mounted in the groove 48 of the shaft body 3 and a large-diameter portion 25 that is a portion of the shaft body 3, whereby movement of the rolling bearing 6 relative to the shaft body 3 in the axial direction is restricted. The internal structure body 10 including the rolling bearing 6 is brought into a state where the internal structure body 10 is interposed in the axial direction between the snap ring 45 mounted in the groove 46 of the case body 2 and the projection portion 21, which is a portion of the case body 2, whereby the case body 2 becomes immovable in the axial direction relative to the rolling bearing 6, which is fixed to the shaft body 3. That is, the snap rings 45 and 47 make the case body 2 and the shaft body 3 immovable in the axial direction with the internal structure body 10 interposed therebetween. The snap rings 45 and 47 are C-shaped snap rings.

As described above, the snap ring 45 at the case body 2 side is detachably mounted in the groove 46 of the case body 2. In a state of being mounted in the case body 2 (groove 46), the snap ring 45 serves as a stopper that restricts relative movement, in the axial direction, of the shaft body 3 and the case body 2 between which the internal structure body 10 including the rolling bearings 5 and 6 and the tubular members 30 are interposed.

Such a state where movement is restricted is a state where assembly is completed, the case body 2 and the shaft body 3 are rotatable relative to each other, and a plurality of different types (two types) of fluids between the case body 2 and the shaft body 3 can be caused to flow through different passages (different fluid passages 4).

In the case where the case body 2 is a stationary member and the shaft body 3 rotates relative to the case body 2, a rotary member includes, in addition to the shaft body 3, the cover member 17, the inner rings 5a and 6a, the balls 5c and 6c, and the snap ring 47, and a stationary member includes, in addition to the case body 2, the outer rings 5b and 6b, the first spacer 31, the second spacer 32, the third spacer 33, and the upper and lower tubular members 30, and the first and second seals 41 and 42.

Here, assembly of the joint 1 will be described. The rolling bearing 5, the two tubular members 30, the spacers 31, 32, and 33, the first seals 41, and the second seals 42 are inserted into the inner side of the case body 2. In addition, the snap ring 45, the rolling bearing 6, and the snap ring 47 are mounted onto the outer side of the shaft body 3. The inner snap ring 47 is fitted into the groove 48, but the outer snap ring 45 is merely placed on a flange 3c of the shaft body 3 (without being fitted into the groove 46), so that the snap ring 45 can be freely moved. Then, the shaft body 3 is inserted into the case body 2, and the snap ring 45 is fitted into the groove 46 of the case body 2. Thereafter, the cover member 17 is mounted to the end portion of the shaft body 3.

Whereas the case body 2 and the shaft body 3 between which the internal structure body 10 is interposed are made immovable in the axial direction relative to each other by mounting the snap ring (stopper) 45 into the groove 46 as described above, the shaft body 3 and the case body 2 are movable in the axial direction relative to each other in a state where the snap ring 45 is disengaged form the groove 46.

In the rotary joint 1 having the above configuration, unlike the conventional rotary joint 90 (see FIG. 4), the third flow passages 13, which connect the first flow passages 11 at the case body 2 side to the second flow passages 12 at the shaft body 3 side, are formed in the tubular members 30 which are members separate from the case body 2. Thus, the case body 91 does not need to have a divided structure (see FIG. 4) as in the conventional art, that is, assembly of the rotary joint 1 is enabled even when the case body 2 is an integral and inseparable tube member.

Here, a specific description will be given. In a state where the snap ring 45 is disengaged from the case body 2, the shaft body 3 and the case body 2 are moved in the axial direction relative to each other with the rolling bearings 5 and 6 and the tubular members 30, etc. interposed therebetween, whereby assembly of the rotary joint 1 is enabled.

Since the case body 2 is composed of an integral and inseparable tube member, bolts (the bolts 94 and 87 in FIG. 4) for integrating the case body 2 as in the conventional art are unnecessary, so that it is possible to make the case body 2 compact.

For making it possible to assemble the rotary joint 1 as described above, the inner diameter of the straight inner peripheral surface 2b of the case body 2 is set so as to be substantially equal to (equal to or slightly larger than) the outer diameter of each portion (the rolling bearings 5 and 6, the tubular members 30, and the spacers 31, 32, and 33) of the internal structure body 10. When each first seal (O-ring) 41 is brought into contact with the inner peripheral surface 2b of the case body 2, the outer diameter of the first seal 41 becomes equal to the inner diameter of the inner peripheral surface 2b. Accordingly, the case body 2 can be assembled to the shaft body 3 by sliding the case body 2 along the outer periphery of the internal structure body 10.

In the present embodiment (see FIG. 2), since each second seal 42 is mounted in the recess portion 38 formed in the tubular member 30, it is made possible to perform an operation of integrating the second seal 42 with the tubular member 30 to mount the second seal 42 at the inner peripheral side of the case body 2.

In addition, each second seal 42 is configured to include the inner cylindrical lip portion 51 and the outer cylindrical lip portion 52 extending from the main body portion 50 as described above. According to this configuration, each second seal 42 and the shaft body 3 are easily moved in the axial direction relative to each other, and in a state where mounting of each second seal 42 is completed, the tubular members 30, which are integrated with the case body 2, and the shaft body 3 are rotatable relative to each other, but it is also possible to ensure sealability between the tubular members 30 and the shaft body 3.

Figure 3:
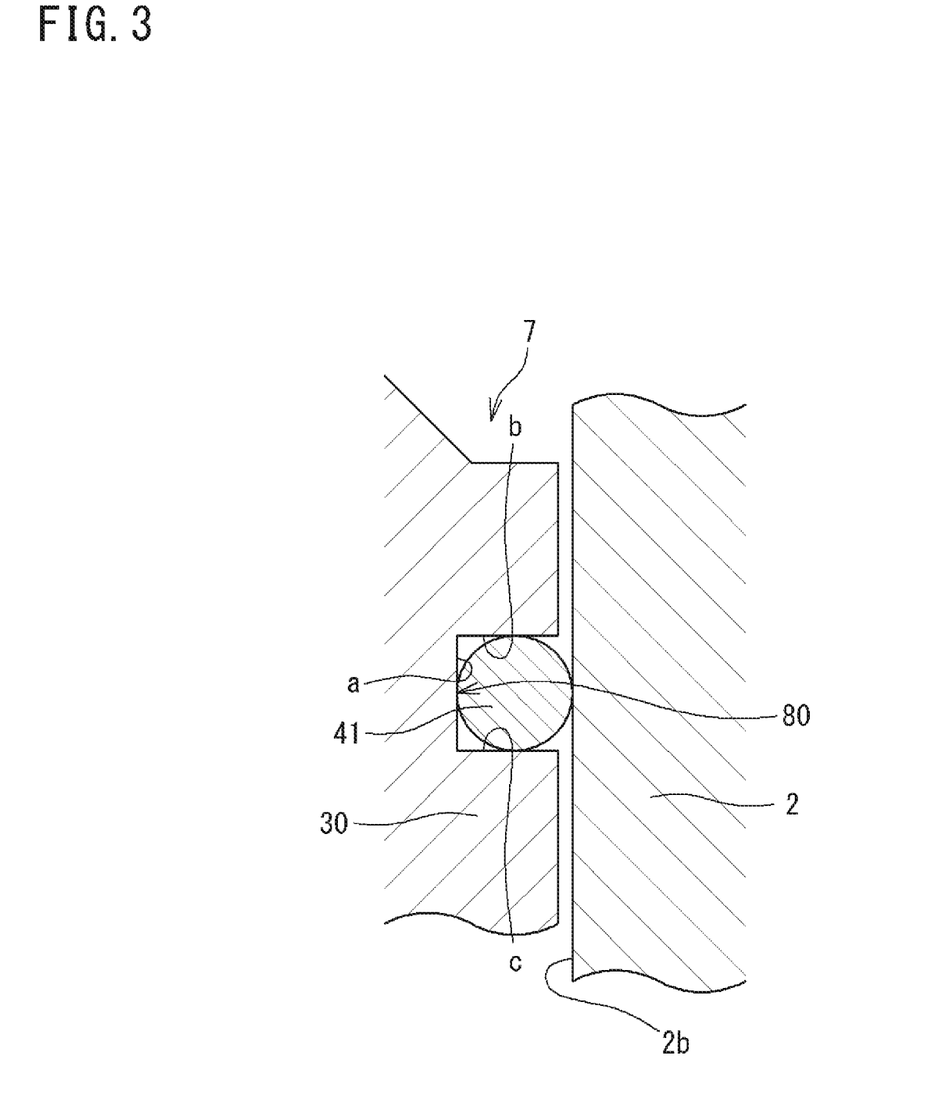
FIG. 3 illustrates the case where a recessed groove having a recessed cross-sectional shape having three inner wall surfaces is a portion for mounting an O-ring (first seal).

According to the present embodiment, it also becomes easy to mount each first seal 41 composed of an O-ring (hereinafter, the first seal 41 is sometimes referred to as O-ring 41). That is, in the case where a groove 80 having a recess shape with a rectangular cross-section having three inner wall surfaces a, b, and c is formed on the outer peripheral surface of the tubular member 30 as shown in FIG. 3 and is a portion for mounting the O-ring (first seal) 41, in order to dispose the O-ring 41 at a predetermined position, the O-ring 41 is fitted into the groove 80 of the tubular member 30, and the case body 2 is moved in the axial direction in this state, whereby the O-ring 41 is moved in the axial direction along the inner peripheral surface 2b of the case body 2. However, in this case, the O-ring 41 easily becomes caught between the case body 2 and the tubular member 30, so that the O-ring 41 may be damaged. However, by forming the inclined surfaces 39 in each tubular member 30 and providing the triangular cross-section space 43 as a portion for mounting each O-ring (first seal) 41 as in the present embodiment (see FIG. 2), it becomes difficult to catch each O-ring (first seal) 41 between the surrounding members during assembling, so that it is possible to prevent damage of the O-ring 41.

Furthermore, since the portion for mounting each O-ring 41 is the triangular cross-section space 43, the O-ring 41 presses the case body 2 in the radial direction, and also presses the tubular member 30 and the spacer 31 (32, 33) in the axial direction. Thus, the O-rings 41 make it possible to enhance the function to prevent the tubular members 30 (and the spacers 31, 32, and 33) from rotating relative to the case body 2. That is, when the shaft body 3 rotates relative to the case body 2, a rotational force is provided from the shaft body 3 to the second seals 42 and the tubular members 30, on which the second seals 42 are mounted, since the second seals 42 are brought into sliding contact with the outer peripheral surface 3b of the shaft body 3. However, a frictional force caused by the pressing by the O-rings 41 can act against this rotational force, so that rotation of the tubular members 30 is prevented.

The embodiment disclosed above is merely illustrative in all aspects and is not restrictive. That is, the rotary joint according to the present invention is not limited to the illustrated form and may be in another form within the scope of the present invention.

In the above embodiment, the number (N) of the fluid passages 4 is "2", but may be a number other than 2. In this case, tubular members 30 of which the number is equal to the number of the fluid passages 4 are provided in the annular space 7. Even when the number of the fluid passages 4 increases, the tubular members 30 all have the same shape, and it is not necessary to produce the ring bodies 99 having a complicated shape as in the conventional art. In addition, although the case body 2 becomes long, the inner peripheral surface 2b suffices to be a straight cylindrical surface, so that production (including machining, etc.) of each component becomes easier as compared to the conventional art, and this can contribute to cost reduction.

The rotary joint 1 according to the present embodiment can be used in relative rotation portions of various rotary apparatuses such as a semiconductor manufacturing apparatus, a medical apparatus, and an apparatus for food, and can be used also in relative rotation portions of other industrial machines.

The foregoing description has been presented for purposes of illustration. It is not intended to be exhaustive or to limit the subject matter to the precise forms disclosed. Persons of ordinary skill in the art will readily recognize and appreciate that modifications and variations are possible in light of, and suggested by, the above teaching. The described embodiments were chosen in order to best explain the principles of the subject matter, its practical application, and to enable others skilled in the art to make use of the same in various embodiments and with various modifications as best suited for the particular application being contemplated.

What is claimed is:

1. A rotary joint comprising: a cylindrical case body having a plurality of first flow passages formed to be opened in an inner peripheral surface thereof and at different positions in an axial direction;
   a shaft body provided inside the cylindrical case body and having a plurality of second flow passages formed to be opened in an outer peripheral surface thereof and at different positions in the axial direction;
   a bearing portion provided in an annular space formed between the case body and the shaft body, the bearing portion supporting the case body and the shaft body such that the case body and the shaft body are rotatable relative to each other;
   a plurality of tubular members provided in the annular space and each having a third flow passage formed for connecting a respective one of the plurality of the first flow passages and a respective one of the plurality of the second flow passages; and
   a first seal configured to prevent a fluid flowing through the respective first flow passage and the third flow passage from leaking through between the case body and the tubular member; and a second seal configured to prevent a fluid flowing through the third flow passage and the respective second flow passage from leaking through between the tubular member and the shaft body, wherein
   the case body is composed of an integral and inseparable tube member that is longer in the axial direction than a dimension, in the axial direction, of an internal structure body including the bearing portion and the tubular members provided in the annular space to be aligned in the axial direction, and
   wherein the first seal is an O-ring, an inclined surface is formed in each tubular member so as to be inclined relative to the inner peripheral surface of the case body, and the O-ring is mounted in a triangular cross-section space formed by the inclined surface, a portion of the inner peripheral surface of the case body, and a portion of a side surface of a member provided adjacently to the tubular member in the axial direction.

2. The rotary joint according to claim 1, wherein the second seal includes an annular main body portion and an inner cylindrical lip portion and an outer cylindrical lip portion extending in the axial direction from a radially inner portion and a radially outer portion of the main body portion, respectively.

3. The rotary joint according to claim 1, wherein the second seal is mounted in a recess portion formed in each tubular member.

4. A rotary joint comprising: a cylindrical case body having a plurality of first flow passages formed to be opened in an inner peripheral surface thereof and at different positions in an axial direction;
- a shaft body provided inside the cylindrical case body and having a plurality of second flow passages formed to be opened in an outer peripheral surface thereof and at different positions in the axial direction;
- a bearing portion provided in an annular space formed between the case body and the shaft body, the bearing portion supporting the case body and the shaft body such that the case body and the shaft body are rotatable relative to each other;
- a plurality of tubular members provided in the annular space and each having a third flow passage formed for connecting a respective one of the plurality of the first flow passages and a respective one of the plurality of the second flow passages; and
- a first seal configured to prevent a fluid flowing through the respective first flow passage and the third flow passage from leaking through between the case body and the tubular member; and a second seal configured to prevent a fluid flowing through the third flow passage and the respective second flow passage from leaking through between the tubular member and the shaft body, wherein
- the case body is composed of an integral and inseparable tube member that is longer in the axial direction than a dimension, in the axial direction, of an internal structure body including the bearing portion and the tubular members provided in the annular space to be aligned in the axial direction, and wherein the second seal includes an annular main body portion and an inner cylindrical lip portion and an outer cylindrical lip portion extending in the axial direction from a radially inner portion and a radially outer portion of the main body portion, respectively.

5. The rotary joint according to claim 4, further comprising a stopper detachably provided in the annular space, wherein relative movement, in the axial direction, of the shaft body and the case body between which the bearing portion and the tubular members are interposed is restricted in a state where the stopper is mounted, and is enabled in a state where the stopper is disengaged.

6. The rotary joint according to claim 4, wherein the second seal is mounted in a recess portion formed in each tubular member.

7. The rotary joint according to claim 6, further comprising a stopper detachably provided in the annular space, wherein relative movement, in the axial direction, of the shaft body and the case body between which the bearing portion and the tubular members are interposed is restricted in a state where the stopper is mounted, and is enabled in a state where the stopper is disengaged.

8. The rotary joint according to claim 7, wherein the first seal is an O-ring, an inclined surface is formed in each tubular member so as to be inclined relative to the inner peripheral surface of the case body, and the O-ring is mounted in a triangular cross-section space formed by the inclined surface, a portion of the inner peripheral surface of the case body, and a portion of a side surface of a member provided adjacently to the tubular member in the axial direction.

9. A rotary joint comprising: a cylindrical case body having a plurality of first flow passages formed to be opened in an inner peripheral surface thereof and at different positions in an axial direction;
- a shaft body provided inside the cylindrical case body and having a plurality of second flow passages formed to be opened in an outer peripheral surface thereof and at different positions in the axial direction;
- a bearing portion provided in an annular space formed between the case body and the shaft body, the bearing portion supporting the case body and the shaft body such that the case body and the shaft body are rotatable relative to each other;
- a plurality of tubular members provided in the annular space and each having a third flow passage formed for connecting a respective one of the plurality of the first flow passages and a respective one of the plurality of the second flow passages;
- a first seal configured to prevent a fluid flowing through the respective first flow passage and the third flow passage from leaking through between the case body and the tubular member; and a second seal configured to prevent a fluid flowing through the third flow passage and the respective second flow passage from leaking through between the tubular member and the shaft body, wherein
- the case body is composed of an integral and inseparable tube member that is longer in the axial direction than a dimension, in the axial direction, of an internal structure body including the bearing portion and the tubular members provided in the annular space to be aligned in the axial direction; and
- comprising a stopper detachably provided in the annular space, wherein relative movement, in the axial direction, of the shaft body and the case body between which the bearing portion and the tubular members are interposed is restricted in a state where the stopper is mounted, and is enabled in a state where the stopper is disengaged,
- wherein the first seal is an O-ring, an inclined surface is formed in each tubular member so as to be inclined relative to the inner peripheral surface of the case body, and the O-ring is mounted in a triangular cross-section space formed by the inclined surface, a portion of the inner peripheral surface of the case body, and a portion of a side surface of a member provided adjacently to the tubular member in the axial direction.

10. The rotary joint according to claim 9, wherein the second seal is mounted in a recess portion formed in each tubular member.

* * * * *